United States Patent
Landolsi et al.

(10) Patent No.: US 10,487,767 B2
(45) Date of Patent: Nov. 26, 2019

(54) METHOD AND SYSTEM FOR MONITORING AIR FILTER CONDITION

(71) Applicant: Ford Global Technologies, LLC, Dearborn, MI (US)

(72) Inventors: Fakhreddine Landolsi, Canton, MI (US); Hassene Jammoussi, Canton, MI (US); Imad Hassan Makki, Dearborn Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 251 days.

(21) Appl. No.: 15/462,677

(22) Filed: Mar. 17, 2017

(65) Prior Publication Data
US 2018/0266354 A1    Sep. 20, 2018

(51) Int. Cl.
| | |
|---|---|
| F02D 41/22 | (2006.01) |
| F02D 41/26 | (2006.01) |
| F02M 35/024 | (2006.01) |
| F02M 35/10 | (2006.01) |
| F02M 35/104 | (2006.01) |
| G01N 15/08 | (2006.01) |
| F02D 41/18 | (2006.01) |
| F02D 41/14 | (2006.01) |

(52) U.S. Cl.
CPC ............ *F02D 41/22* (2013.01); *F02D 41/18* (2013.01); *F02D 41/26* (2013.01); *F02M 35/024* (2013.01); *F02M 35/104* (2013.01); *F02M 35/10386* (2013.01); *F02D 2041/1416* (2013.01); *F02D 2041/1417* (2013.01); *F02D 2200/0406* (2013.01); *F02D 2200/0414* (2013.01); *F02D 2200/703* (2013.01); *G01N 15/0826* (2013.01); *G01N 2015/084* (2013.01)

(58) Field of Classification Search
None
See application file for complete search history.

(56) References Cited

U.S. PATENT DOCUMENTS

| | | |
|---|---|---|
| 5,604,306 A | 2/1997 | Schricker |
| 5,606,311 A | 2/1997 | Polidan et al. |
| 7,032,573 B2 * | 4/2006 | Ardisana .............. F02D 41/18 |
| | | 123/198 E |

(Continued)

FOREIGN PATENT DOCUMENTS

| | | | |
|---|---|---|---|
| DE | 102009018704 A1 | 10/2010 | |
| FR | 2980522 A3 * | 3/2013 | ......... F02M 35/1038 |

OTHER PUBLICATIONS

Landolsi, Fakhreddine, et al., "Air Filter Diagnostics & Prognostics in Naturally Aspired Engines," Ford Motor Company Research & Innovation Center, 5 pages.

(Continued)

*Primary Examiner* — Thomas G Black
*Assistant Examiner* — Demetra R Smith-Stewart
(74) *Attorney, Agent, or Firm* — Geoffrey Brumbaugh; McCoy Russell LLP (57) ABSTRACT

Methods and systems are provided for determining condition of an air filter coupled to an intake passage of an engine system. In one example, a method may include estimating a resistance of the air filter based on a manifold air charge value. The manifold air charge value may be either a mass air flow or a manifold air pressure.

14 Claims, 5 Drawing Sheets

(56) References Cited

U.S. PATENT DOCUMENTS

| | | | |
|---|---|---|---|
| 7,441,449 B2* | 10/2008 | Wang | F02D 35/0023 73/114.31 |
| 7,444,234 B2* | 10/2008 | Bauerle | F02M 35/09 123/361 |
| 8,573,040 B2* | 11/2013 | Guzman | F02M 35/024 73/114.31 |
| 2003/0028335 A1* | 2/2003 | Wild | F02M 35/09 702/50 |
| 2003/0052791 A1 | 3/2003 | Reinhardt et al. | |
| 2008/0229720 A1 | 9/2008 | Benscoter et al. | |
| 2011/0185895 A1 | 8/2011 | Freen | |
| 2013/0036804 A1 | 2/2013 | Uehara | |
| 2014/0360362 A1* | 12/2014 | Peters | F01N 3/037 95/28 |
| 2018/0202398 A1* | 7/2018 | Jammoussi | F02M 35/024 |
| 2018/0204393 A1* | 7/2018 | Landolsi | B60L 11/1851 |

OTHER PUBLICATIONS

Innocentini, Murilo D. M., et al., "Assessment of Forchheimer's Equation to Predict the Permeability of Ceramic Foams," Journal of the American Ceramic Society, vol. 82, Issue 7, Jul. 1999, pp. 1945-1948, 4 pages.

Jammoussi, Hassene, et al., "Secondary System and Method for Controlling an Engine," U.S. Appl. No. 15/216,409, filed Jul. 21, 2016, 30 pages.

* cited by examiner

METHOD AND SYSTEM FOR MONITORING AIR FILTER CONDITION

FIELD

The present description relates generally to methods and systems for diagnosing condition of an air filter coupled to an intake passage of an engine.

BACKGROUND/SUMMARY

Air filters positioned within or as part of an air intake system for an engine provide filtered air for the engine. The air filters may clog due to accumulation of dust or frost. Clogged air filter may lead to decreased manifold air pressure, and deteriorate fuel economy and drivability. Monitoring air filter condition may provide an early indication of the remaining useful life of the air filter and help car owner plan maintenance ahead of time.

Other attempts to address air filter clogging include determining filter clogging based on pressure difference across the air filter. One example approach is shown by Freen et al. in U.S. 20110185895A1. Therein, a differential pressure sensor measures a pressure differential between a first pressure upstream of the air filter and a second pressure downstream of the air filter. Filter condition is then determined by comparing the pressure differential with a baseline pressure differential.

However, the inventors herein have recognized potential issues with such systems. As one example, Freen requires a battery powered probe to measure the pressure differential across the air filter. In naturally aspired engines, differential pressure sensor is generally not present around the air filter. The additional probe in Freen may add complexity and cost to the engine system. Further, Freen requires re-calibration of the baseline pressure differential by a user whenever a new filter is installed. If the re-calibration is not timely performed, Freen's method may lead to incorrect estimation of filter condition.

In one example, the issues described above may be addressed by a method comprising: routing air through an air filter into a manifold; during steady state condition, estimating an air filter resistance based on an air charge value in the manifold, the air filter resistance being inversely proportional to the square of a mass air flow through the air filter; and indicating air filter condition based on the air filter resistance. In this way, air filter clogging may be determined during steady state condition without requiring additional sensor.

As one example, an observer may be constructed for estimating an air filter resistance of an air filter coupled to the intake passage of an engine system. Air filter condition may be determined based on the air filter resistance. For example, filter clogging may be determined in response to air filter resistance higher than a threshold. The air filter resistance may be inversely proportional to the square of a mass air flow through the air filter and proportional to a pressure difference across the air filter. As such, the air filter resistance may characterize filter clogging regardless filter geometry or material properties. In other words, air filter condition may be determined by the air filter resistance even when different types of filters may be used. The air filter resistance may be estimated based on an air charge value in the manifold via the observer. In non-boosted applications, either a mass air flow (MAF) sensor downstream of the air filter or a manifold air pressure (MAP) sensor downstream of a throttle may present in the engine system for monitoring the air charge. During steady state condition, the mass air flow through the intake manifold may be the same as the mass air flow through the air filter and the mass air flow through the throttle. Thus, based on availability of the sensor, during steady state condition, the manifold air charge value may be a MAF measured by the MAF sensor or a MAP measured by the MAP sensor. If the manifold air charge value is the MAF, the observer may estimate system states including the resistance of the air filter, a pressure immediately downstream of the air filter, and the MAP simultaneously. If the manifold air charge value is the MAP, the observer may estimate system states including the resistance of the air filter and the pressure immediately downstream of the air filter simultaneously. In this way, air filter condition may be determined based on the manifold air charge value measured by the sensor already existed in the engine system. The observer may estimate the resistance of the air filter without the knowledge of throttle position. Further, air filter condition may be determined online without interrupting engine operation.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

DETAILED DESCRIPTION

Figure 1:
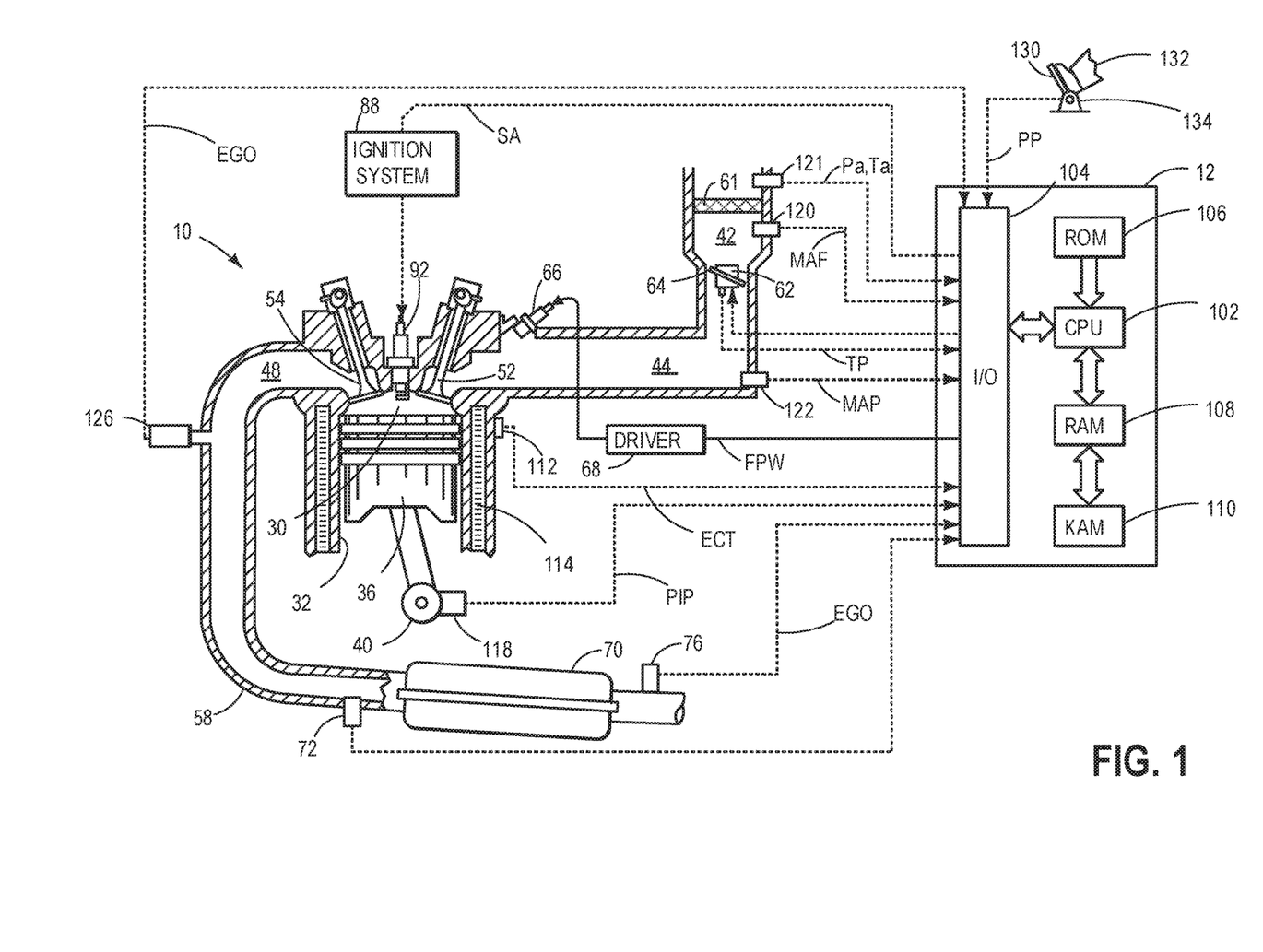
FIG. 1 shows a schematic diagram of an example cylinder of a multi-cylinder engine system with an air filter coupled in an intake manifold.
Figure 2:
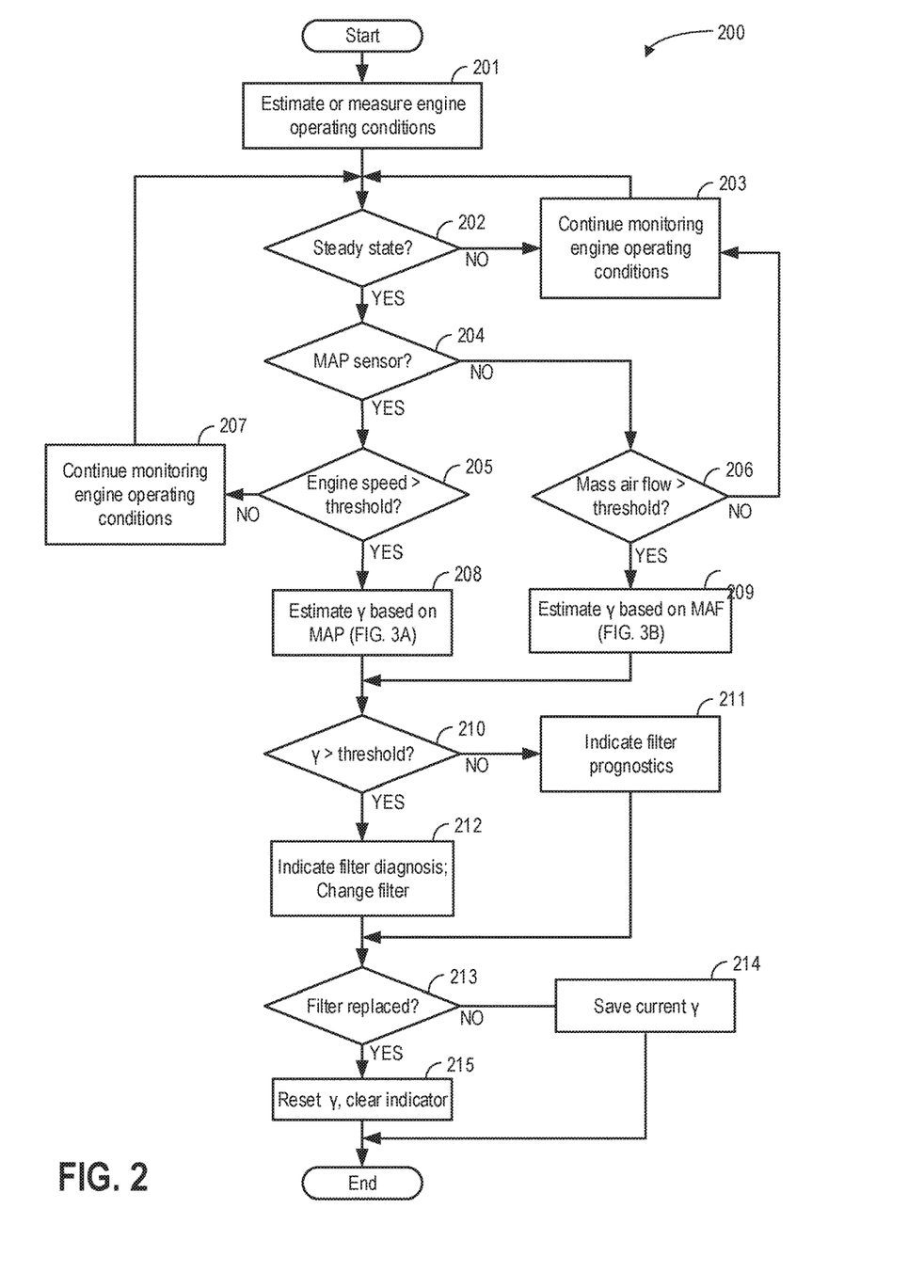
FIG. 2 shows an example method for diagnosing the air filter condition via an observer.
Figure 3A:
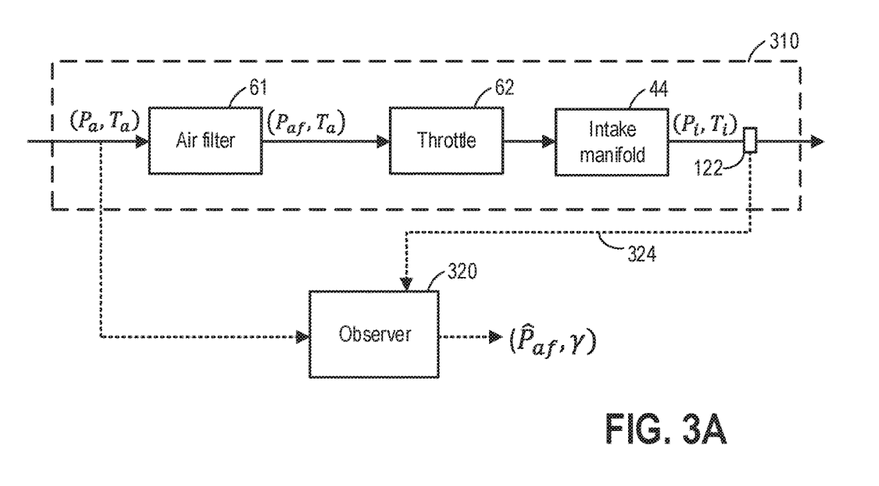
FIG. 3A shows a first embodiment of the observer.
Figure 3B:
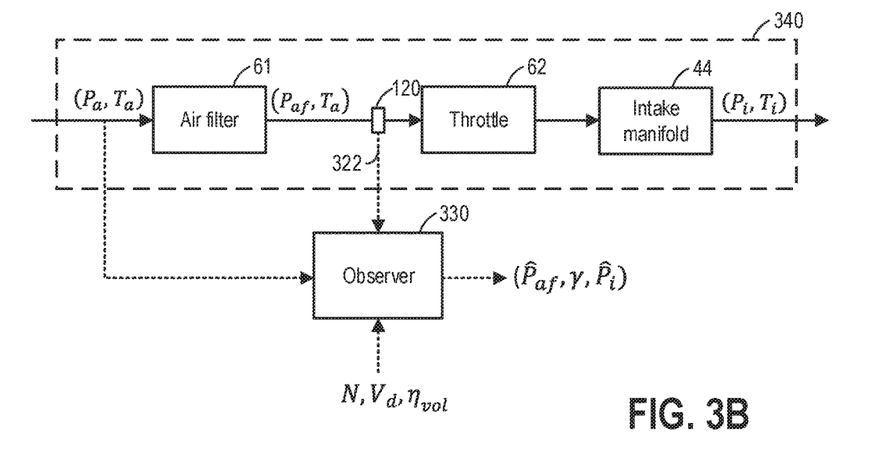
FIG. 3B shows a second embodiment of the observer.
Figure 4:
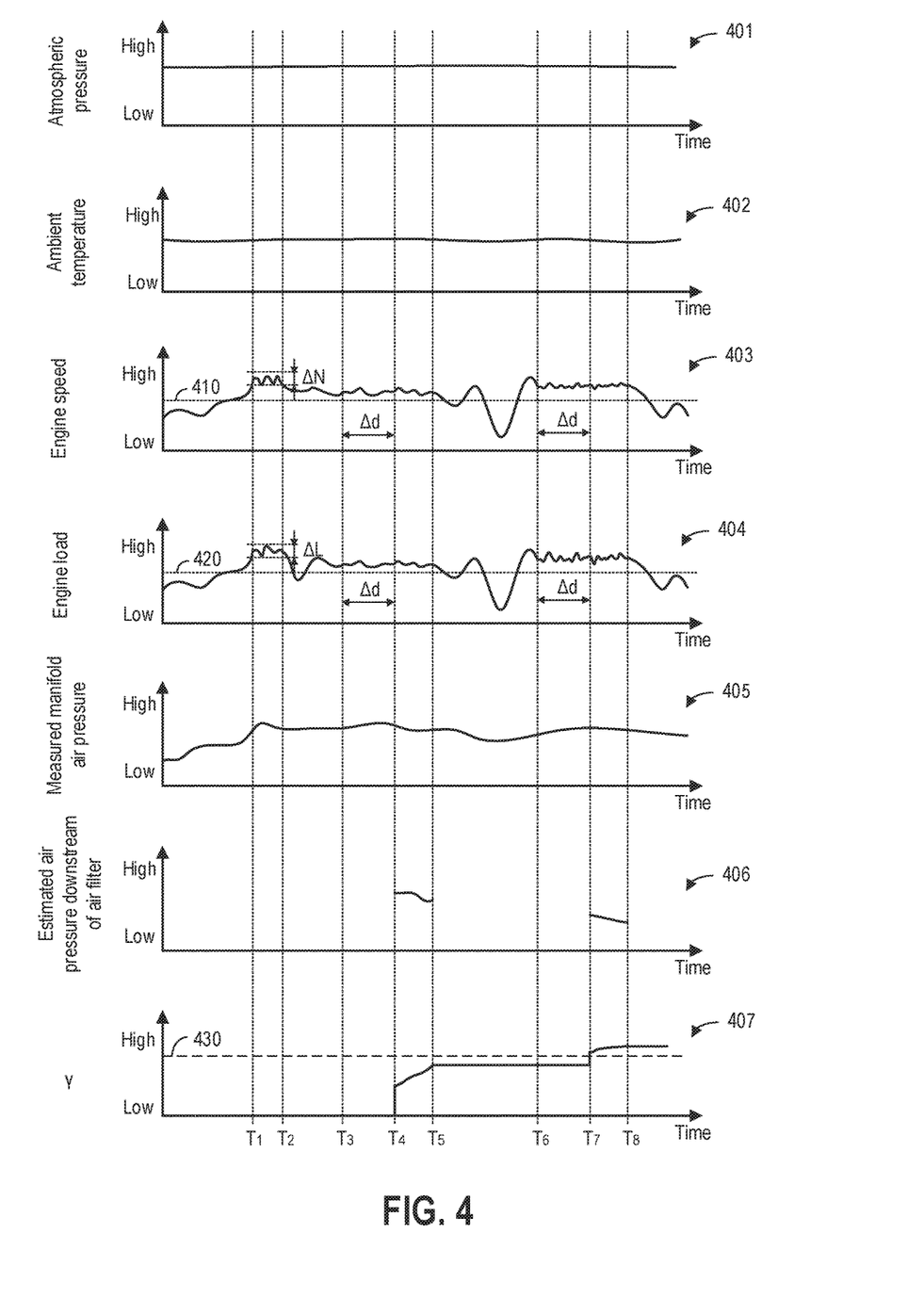
FIG. 4 shows parameter timelines when determining the air filter condition via the first embodiment of the observer.
Figure 5:
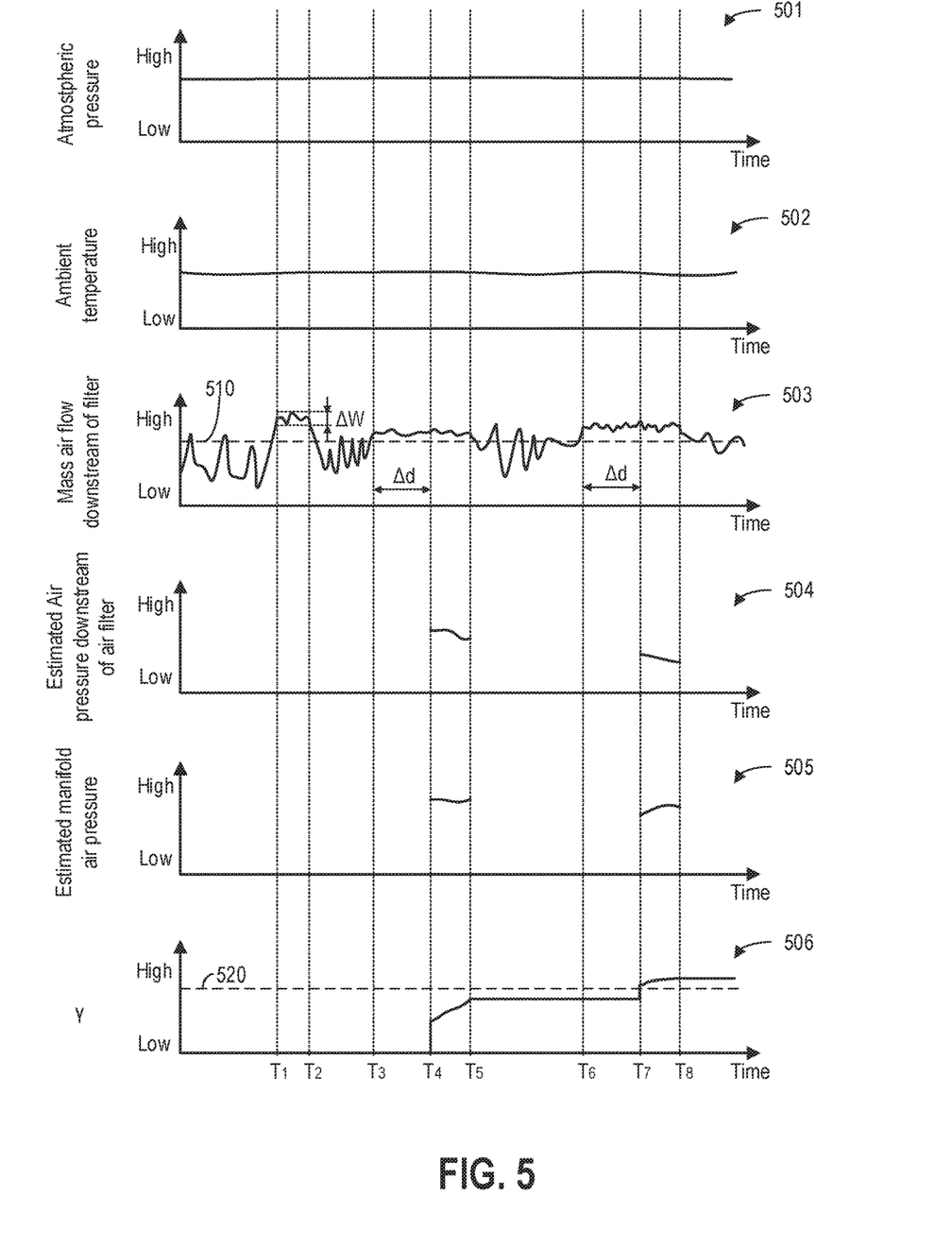
FIG. 5 shows parameter timelines when determining the air filter condition via the second embodiment of the observer.

The following description relates to systems and methods for determining the condition of an air filter coupled to the intake passage of a non-boosted engine system, such as an engine system shown in FIG. 1. The condition of the air filter may be characterized by an air filter resistance. FIG. 2 shows an example method of estimating the air filter resistance based on a manifold air charge value via an observer during steady state condition. If a manifold air pressure (MAP) sensor is present in the engine system, a first embodiment of the observer may estimate system states including the air pressure immediately downstream of the air filter and the resistance of the air filter based on a measured MAP, as shown in FIG. 3A. Variation of parameters when determining the air filter condition via the first embodiment of the observer is shown in FIG. 4. If a mass air flow (MAF) sensor downstream of the air filter is present in the engine system, a second embodiment of the observer may estimate system states including the air pressure immediately downstream of the air filter, the resistance of the air filter, and the MAP based on the measured MAF, as shown in FIG. 3B. Variation of parameters when determining the air filter condition via the second embodiment of the observer is shown in FIG. 5.

Turning to FIG. 1, a schematic diagram showing one cylinder of multi-cylinder engine 10, which may be included in a propulsion system of a vehicle, is shown. Engine 10 may be controlled at least partially by a control system including controller 12 and by input from a vehicle operator 132 via an input device 130. In this example, input device 130 includes an accelerator pedal and a pedal position sensor 134 for generating a proportional pedal position signal PP. Combustion chamber 30 (also termed, cylinder 30) of engine 10 may include combustion chamber walls 32 with piston 36 positioned therein. Piston 36 may be coupled to crankshaft 40 so that reciprocating motion of the piston is translated into rotational motion of the crankshaft. Crankshaft 40 may be coupled to at least one drive wheel of a vehicle via an intermediate transmission system (not shown). Further, a starter motor may be coupled to crankshaft 40 via a flywheel (not shown) to enable a starting operation of engine 10.

Combustion chamber 30 may receive intake air from intake manifold 44 via intake passage 42 and may exhaust combustion gases via exhaust manifold 48. Intake manifold 44 and exhaust manifold 48 can selectively communicate with combustion chamber 30 via respective intake valve 52 and exhaust valve 54. In some embodiments, combustion chamber 30 may include two or more intake valves and/or two or more exhaust valves. Ambient air may be naturally aspirated into combustion chamber 30 sequentially via intake passage 42 and intake manifold 44. After combustion, exhaust gases exits combustion chamber into atmosphere via the exhaust manifold 48 and emission control device 70. As such, gas flow through the engine system starts from intake passage 42, and ends at emission control device 70.

Fuel injector 66 is shown arranged in intake manifold 44 in a configuration that provides what is known as port injection of fuel into the intake port upstream of combustion chamber 30. Fuel injector 66 may inject fuel in proportion to the pulse width of signal FPW received from controller 12 via electronic driver 68. Fuel may be delivered to fuel injector 66 by a fuel system (not shown) including a fuel tank, a fuel pump, and a fuel rail. In some embodiments, combustion chamber 30 may alternatively or additionally include a fuel injector coupled directly to combustion chamber 30 for injecting fuel directly therein, in a manner known as direct injection.

Intake passage 42 may include an air filter 61 for filtering intake air passing through the intake passage. A throttle 62 having a throttle plate 64 may be coupled to the intake passage downstream of air filter 61. In this particular example, the position of throttle plate 64 may be varied by controller 12 via a signal provided to an electric motor or actuator included with throttle 62, a configuration that is commonly referred to as electronic throttle control (ETC). In this manner, throttle 62 may be operated to vary the intake air provided to combustion chamber 30 among other engine cylinders. The position of throttle plate 64 may be provided to controller 12 by throttle position signal TP. A MAF sensor 120 may couple between air filter 61 and throttle 62 for providing a MAF signal to controller 12. A MAP sensor 122 may be coupled to intake manifold 44 downstream of throttle 62 for providing respective MAP signal to controller 12. Sensors 121 may be coupled to the intake system for measuring atmospheric pressure Pa and ambient temperature Ta. In another embodiment, the atmospheric pressure may be inferred. In yet another embodiment, the atmospheric pressure may be determined based on MAP measurements during very low engine speeds.

Ignition system 88 can provide an ignition spark to combustion chamber 30 via spark plug 92 in response to spark advance signal SA from controller 12, under select operating modes. Though spark ignition components are shown, in some embodiments, combustion chamber 30 or one or more other combustion chambers of engine 10 may be operated in a compression ignition mode, with or without an ignition spark.

Exhaust gas sensor 126 is shown coupled to exhaust passage 58 upstream of emission control device 70. Sensor 126 may be any suitable sensor for providing an indication of exhaust gas air-fuel ratio such as a linear oxygen sensor or UEGO (universal or wide-range exhaust gas oxygen), a two-state oxygen sensor or EGO, a HEGO (heated EGO), a NOx, HC, or CO sensor. Emission control device 70 is shown arranged along exhaust passage 58 downstream of exhaust gas sensor 126. Device 70 may be a three way catalyst (TWC), NOx trap, various other emission control devices, or combinations thereof. In some embodiments, during operation of engine 10, emission control device 70 may be periodically reset by operating at least one cylinder of the engine within a particular air/fuel ratio. Full-volume exhaust gas sensor 76 is shown coupled to exhaust passage 58 downstream of emission control device 70. Other sensors 72 such as an air mass flow (AM) and/or a temperature sensor may be disposed upstream of emission control device 70 to monitor the AM and temperature of the exhaust gas entering the emission control device.

Controller 12 is shown in FIG. 1 as a microcomputer, including microprocessor unit 102, input/output ports 104, an electronic storage medium for executable programs and calibration values shown as read only memory 106 in this particular example, random access memory 108, keep alive memory 110, and a data bus. Controller 12 may receive various signals from sensors coupled to engine 10, in addition to those signals previously discussed, including measurement of inducted mass air flow (MAF) from mass air flow sensor 120; engine coolant temperature (ECT) from temperature sensor 112 coupled to cooling sleeve 114; a profile ignition pickup signal (PIP) from Hall effect sensor 118 (or other type) coupled to crankshaft 40; throttle position (TP) from a throttle position sensor; airmass and/or temperature of the exhaust gas entering the catalyst from sensor 72; exhaust gas air-fuel ratio post-catalyst from sensor 76; and absolute manifold pressure signal, MAP, from sensor 122. Engine speed signal, RPM, may be generated by controller 12 from signal PIP. Manifold pressure signal MAP from a manifold pressure sensor may be used to provide an indication of vacuum, or pressure, in the intake manifold. Note that various combinations of the above sensors may be used, such as a MAF sensor without a MAP sensor, or vice versa. During stoichiometric operation, the MAP sensor can give an indication of engine torque. Further, this sensor, along with the detected engine speed, can provide an estimate of charge (including air) inducted into the cylinder. In one example, sensor 118, which is also used as an engine speed sensor, may produce a predetermined number of equally spaced pulses for each revolution of the crankshaft. Additionally, controller 12 may communicate with a cluster display device, for example to alert the driver of faults in the engine or exhaust after-treatment system.

The controller 12 receives signals from the various sensors of FIG. 1 and employs the various actuators of FIG. 1 to adjust engine operation based on the received signals and instructions stored on a memory of the controller. For example, adjusting engine air intake includes adjusting an actuator of throttle 62 to adjust the angle of throttle plate 64.

FIG. 2 shows an example method of estimating air filter condition based on a manifold air charge value during steady state condition. The manifold air charge value may be a MAF downstream of the air filter or a MAP. Based on the type of sensor presented in the engine system, different observers may be constructed for estimating the air filter resistance. If a MAP sensor is available, the observer may estimate two system states including air filter resistance and air pressure immediately downstream of the air filter. If a MAF sensor is available, the observer may estimate three system states including the air filter resistance, the air pressure immediately downstream of the air filter, and the MAP.

Instructions for carrying out method 200 and the rest of the methods included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 201, engine operating conditions may be determined by a controller (such as controller 12 of FIG. 1). The controller acquires measurements from various sensors in the engine system and estimates operating conditions including atmospheric pressure, ambient temperature, engine speed, and engine load. The controller may also estimate engine displacement volume and volumetric efficiency based on inputs from the sensors. If a MAF sensor is coupled to the intake passage downstream of the air filter and upstream of the throttle, the controller may monitor MAF. If a MAP sensor is coupled to the intake manifold, the controller may monitor MAP.

At 202, method 200 determines whether the engine is in steady state operation. In one embodiment, steady state condition may be determined based on engine speed and engine load. For example, steady state operation may be determined if the variation of engine speed is within a first threshold and the variation of engine load is within a second threshold for a predetermined duration. In another embodiment, steady state condition may be determined by either one of engine speed or engine load. In another embodiment, if the MAF sensor is available (such as MAF measured by sensor 120 of FIG. 1), steady state operation may be determined based on MAF. For example, steady state operation may be determined if the variation of the MAF is within a threshold for a predetermined duration. In yet another example, the steady state condition may be assessed based on throttle angle variations by setting proper thresholds. If the engine is in steady state operation, method 200 moves to 204. Otherwise, method 200 moves to 203, and continues monitoring engine operating conditions.

At 204, method 200 determines whether the engine system includes a MAP sensor. If the MAP sensor is present in the system, method 200 moves to 205. If the manifold air pressure sensor is not present in the system, method 200 moves to 206.

At 205, method 200 determines whether the air filer resistance may be estimated by an observer. If the engine speed is higher than a predetermined threshold, method 200 moves to 208, and estimates air filter resistance based on MAP. Otherwise, method 200 moves to 207, and continues monitoring engine operating conditions. Alternatively, engine load or a combination of the engine speed and the engine load may be used to determine whether the air filter resistance can be estimated by the observer.

At 208, the air filter resistance is estimated based on MAP via an observer. FIG. 3A illustrates one embodiment of the observer. The intake air path 310 includes air filter 61, throttle 62, and intake manifold 44. Solid arrows indicate direction of air flow. Each component of intake air path 310 may be characterized by mass flow, pressure, and temperature of the air passing through the component. As such, different components of the intake air path may be modeled as control volumes that act on the pressure and temperature of the flowing air.

As an example, air filter 61 acts as a restriction to the flowing air that is assumed to be an incompressible fluid. Air entering air filter 61 is at atmospheric pressure $P_a$ and ambient temperature $T_a$. Air exiting air filter 61 is at pressure $P_{af}$ and temperature $T_a$. The filter is considered not to affect the temperature of the air passing through it (i.e. the input and output air temperature are both $T_a$). Assuming a constant Reynolds number for the air flow, pressure drop across the air filter $\Delta p$ can be described as a function of the mass flow and the air temperature entering the air filter:

$$\Delta p = \gamma \frac{T_a}{P_a} W_{af}^2 \qquad \text{Equation 1}$$

where the pressure drop is the difference between the input and out pressure of the air filter (i.e. $\Delta p = P_a - P_{af}$); $\gamma$ represents the air filter resistance; and $W_{af}$ represents MAF through the filter. The air filter resistance $\gamma$ has an unit of $$\left[\frac{P_a^2 s^2}{K k g^2}\right].$$

The air niter resistance encapsulates the material and geometrical properties of the filter. As such, air filter health may be characterized by the air filter resistance. For example, increased air filter resistance indicates filter clogging and reduced air filter life.

With known pressure drop $\Delta p$ and the temperature before the air filter restriction, the mass flow $W_{af}$ may be determined by inverting Equation 1. For small pressure drops, $W_{af}$ may be linearized to reduce the corresponding derivative $\partial W/\partial \Delta p$. As such, in the region where $\Delta p$ approaches zero, $W_{af}$ may have a linear extension ensuring that the model is Lipschitz. The extension models the transition from laminar to turbulent conditions. Based on the above assumptions, the $W_{af}$ may be presented as a function of the pressure drop and air filter resistance:

$$W_{af} = \begin{cases} \sqrt{p_a \frac{\Delta p}{\gamma T_a}} & \text{if } \Delta p > p_{lin} \\ \sqrt{\frac{p_a}{\gamma T_a}} \frac{\Delta p}{\sqrt{p_{lin}}} & \text{for } 0 \leq \Delta p \leq p_{lin} \\ 0 & \text{for } \Delta p < 0 \end{cases} \qquad \text{Equation 2}$$

wherein $p_{lin}$ denotes a predetermined critical pressure.

Observer 320 may estimate the air filter resistance based on the measured MAP 324 sensed by pressure sensor 122. In one example, the observer outputs estimated air pressure $\hat{P}_{af}$ immediately downstream of the air filter and air filter resistance $\gamma$, based on inputs including atmospheric pressure, ambient temperature, and MAP. The optimal observer may have a state space form of:

$$\begin{cases} x_k = f(x_{k-1}) + w_k \\ z_k = h(x_k) + v_k \end{cases} \quad \text{Equation 3}$$

wherein function $f(\cdot)$ predicts system state x at time k based on the state at a previous time k−1; function $h(\cdot)$ computes measurement z based on system state x; $w_k$ and $v_k$ are process and observation noises at time k, respectively.

When $W_{af}$ is higher than the predetermined critical pressure, system equation for control block 310 may be expressed as:

$$\begin{cases} W_{af} = \sqrt{P_a \dfrac{\Delta p}{\gamma T_a}} \\ W_t = \dfrac{P_{af}}{\sqrt{RT_a}} C_d A(\alpha) \Psi(\Pi) \end{cases} \quad \text{Equation 4}$$

wherein $W_t$ denotes the MAF through the throttle; R denotes gas constant; $C_d$ denotes discharge coefficient; $A(\cdot)$ denotes function for calculating effective area of throttle plate based on throttle angle $\alpha$; and $\Pi$ is defined as the ratio between output and input pressure of the throttle $$\left( \text{i.e., } \Pi = \frac{P_i}{P_{af}} \right).$$

The flow characteristic function is defined as:

$$\Psi(\cdot) = \begin{cases} \Pi^{1/\kappa} \sqrt{\dfrac{2\kappa}{\kappa-1}\left(1 - \Pi^{\kappa-1/\kappa}\right)} & \text{if } \Pi \leq 0.528 \\ \kappa^{1/2}\left(\dfrac{2}{\kappa+1}\right)^{(\kappa+1)/2(\kappa-1)} & \text{otherwise} \end{cases} \quad \text{Equation 5}$$

wherein $\kappa$ denotes the air bulk modulus. During steady state condition, MAF through the air filter equals to the MAF through the throttle (i.e., $W_{af} = W_t$).

The system equation (Equation 4) may be converted into the state space form as shown in Equation 3, with system states including air filter resistance and air pressure immediately downstream of the air filter. As such, system state and measurement vector may be presented as $x = [\gamma P_{af}]^T$ and $z = [W_{af} W_t]^T$, respectively.

A standard Extended Kalman Filter may then be used to estimate the system states. The corresponding prediction and update equations are in the following form:

$$\begin{cases} \hat{x}_{k|k-1} = f(\hat{x}_{k-1|k-1}, u_{k-1}) \\ P_{k|k-1} = F_{k-1} P_{k-1|k-1} F_{k-1}^T + Q_{k-1} \end{cases} \quad \text{Equation 6}$$

$$\begin{cases} \tilde{y}_k = z_k - h(\hat{x}_{k|k-1}) \\ S_k = H_k P_{k|k-1} H_k^T + R_k \\ K_k = P_{k|k-1} H_k^T S_k^{-1} \\ \hat{x}_{k|k} = \hat{x}_{k|k-1} + K_k \tilde{y}_k \\ P_{k|k} = (I - K_k H_k) P_{k|k-1} \end{cases} \quad \text{Equation 7}$$

wherein u denotes control inputs; Q denotes the process noise covariance matrix; and $F_{k-1}$ and $H_k$ are the state transition and observation jacobians:

$$F_{k-1} = \left. \frac{\partial f}{\partial x} \right|_{\hat{x}_{k-1|k-1}, u_{k-1}} \quad \text{Equation 8}$$

$$H_k = \left. \frac{\partial h}{\partial x} \right|_{\hat{x}_{k|k-1}}$$

FIG. 4 illustrates variation of parameters over time while using the observer shown in FIG. 3A for estimating air filter resistance.

Turning back to FIG. 2, at 206, method 200 determines whether MAF measured by the MAF sensor downstream of the air filter is higher than a predetermined threshold. If the answer is yes, method 200 moves to 209, and estimates air filter resistance based on MAF. If the answer is no, method 200 moves to 203, and continues monitoring engine operating conditions.

At 209, the air filter resistance is estimated based on the MAF downstream of the air filter via an observer. On embodiment of the observer 330 is shown in FIG. 3B. Intake air path 340 includes a MAF sensor 120 coupled between air filter 61 and throttle 62, instead of a MAP sensor downstream of the air filter (as shown in FIG. 3A). Observer 330 outputs estimated air pressure $\hat{P}_{af}$ immediately downstream the air filter, air filter resistance $\gamma$, and estimated MAP $\hat{P}_i$ based on inputs including atmospheric pressure $P_a$, ambient temperature $T_a$, MAF 322, engine speed N, displacement volume $V_d$, and volumetric efficiency $\eta_{vol}$. Observer 330 may share the same state space form (Equation 3) as observer 320 of FIG. 3A. System equations for intake air path 340 may be shown as follows:

$$\begin{cases} W_{af} = \sqrt{P_a \dfrac{\Delta p}{\gamma T_a}} \\ W_t = \dfrac{P_{af}}{\sqrt{RT_a}} C_d A(\alpha) \Psi(\Pi) \\ W_e = \dfrac{P_a V_d N}{120\, RT_a} \eta_{vol} \end{cases} \quad \text{Equation 8}$$

where $W_e$ denotes the MAF through the intake manifold; $V_d$ denotes displacement volume; and $\eta_{vol}$ denotes volumetric efficiency. During steady state condition, MAF through the air filter, throttle, and the manifold are the same as the MAF 322 measured by sensor 120 (i.e., $W_{af} = W_t = W_e = W$). Since the MAP is not measured, system equations of intake air path 340 require an additional intake manifold equation (the third equation in Equation 8) comparing to Equation 4. The system states of observer 330 are $x = [\gamma P_{af} P_i]^T$, and the measurement vector is given by $z = [W_{af} W_t W_e]^T$. Similar to observer 320 of FIG. 3A, the system states of observer 330 may be estimated as a standard Extended Kalman Filter. FIG. 5 shows variations of parameters over time while estimating air filter resistance with observer 330.

Turning back to FIG. 2, at 210, method 200 compares the estimated air filter resistance with a predetermined threshold. If the air filter resistance is higher than the threshold, method 200 moves to 212 to indicate filter diagnosis. If the air filter resistance is not higher than the threshold, method 200 moves to 211 to indicate filter prognostics.

At 211, filter prognostics may be determined based on the level of air filter resistance. The filter prognostics may further depends on the history of air filter resistance and drive statistics. For example, the history of air filter resistance may be the filter life time for the same type of filter within the same type of engine system. The driver statistics may include previous and future engine operating parameters (such as engine speed and engine load), road conditions (such as road grade), and ambient conditions (such as weather and altitude). The filter prognostics may include the time to change the air filter, distance to change the filter, and/or remaining filter life.

At 212, filter condition may be determined and indicated to the driver. For example, an indicator on the displaying device may light up. Further, in response to high air filter resistance, the air filter may be replaced.

At 213, method 200 determines if the filter has been replaced. If the answer is yes, at 215, the controller may reset the air filter resistance and clear any indicators that has been set. Otherwise, the controller may save current estimated air filter resistance in the memory at 214.

FIG. 4 shows variation of parameters over time while using observer 320 of FIG. 3A to estimate air filter resistance based on a sensed MAP. Parameters include atmospheric pressure 401, ambient temperature 402, engine speed 403, engine load 404, MAP 405, air pressure downstream of air filter 406, and air filter resistance 407 are shown in the figure. The x-axes indicate time and increase as indicated by the arrow. The observer may determine whether the engine is in steady state operation and suitable for filter resistance estimation based on estimated engine speed and/or estimated engine load. The observer may be implemented by a controller, such as controller 12 of FIG. 1.

At $T_1$, engine speed 403 exceeds threshold 410, and engine load 404 exceeds threshold 420. From $T_1$ to $T_2$, the variation of engine speed is less than a predetermined threshold $\Delta N$, and the variation of engine load is less than a predetermined threshold $\Delta L$. At $T_2$, both engine speed and engine load decreases. Since the time duration from $T_1$ to $T_2$ is less than a predetermined threshold $\Delta d$, the controller determines that the engine is not in steady state operation, and the observer cannot operate. As such, air pressure downstream of the air filter 406 is unavailable, and air filter resistance 407 is zero.

From $T_3$ to $T_4$, engine speed and the engine load are higher than threshold 410 and 420, respectively. Further, since the variation of the engine speed and engine load are within their respective thresholds ($\Delta N$ and $\Delta L$) for a duration of $\Delta d$, at $T_4$, the controller determines that entry conditions for operating the observer are met, and starts to estimate air pressure 406 and air filter resistance 407 based on MAP 405, atmospheric pressure 401, and ambient temperature 402. Since estimated air filter resistance 407 is lower than threshold 430, the controller may estimate and indicate prognostics of the filter (such as remaining filter life time) based on the level of the air filter resistance.

At $T_5$, in response to an increase in the variation of engine speed and engine load, the controller stops running the observer. As a result, the air filter resistance is stopped being updated.

From $T_6$ to $T_7$, engine speed and engine load are higher than predetermined thresholds, and their variations are low for a duration of $\Delta d$. As such, observer resumes its operation, and starts to estimate air pressure 406 and the air filter resistance 407.

At $T_7$, in response to estimated air filter resistance higher than threshold 430, the controller may indicate filter clogging and requires the driver to replacing the air filter. Due to increased filter clogging, estimated air pressure immediately downstream of the air filter decreases comparing to the period from $T_4$ to $T_5$. When the filter is replaced, controller may reset the air filter resistance to zero.

FIG. 5 shows variation of parameters over time while using observer 330 of FIG. 3B to estimate air filter resistance based on a sensed MAF. The parameters include atmospheric pressure 501, ambient temperature 502, MAF 503 downstream of the filter, air pressure 504 downstream of the filter, MAP 505, and air filter resistance 506. The x-axes indicate time and increase as indicated by the arrow. The observer may determine whether the engine is in steady state operation and suitable for filter resistance estimation based on the sensed MAF via a sensor (such as sensor 120 of FIG. 1). The observer may be implemented by a controller (such as controller 12 of FIG. 1).

From $T_1$ to $T_2$, MAF 503 is higher than threshold 510, and the variation of the MAF is less than a predetermined threshold $\Delta W$. At $T_2$, MAF decreases, and the variation of the MAF exceeds threshold $\Delta W$. Since the duration from $T_1$ to $T_2$ is less than a predetermined time duration $\Delta d$, the engine is not in steady state condition. Thus, observer 330 cannot operate. There is no estimation of air pressure 504 downstream of the air filter or the MAP 505. The air filter resistance 506 is zero.

From $T_3$ to $T_4$, MAF 503 is higher than threshold 510, and its variation is within threshold $\Delta W$. Thus, at $T_4$, the controller determines that the engine is at steady state operation. In response to steady state condition, observer 330 estimates air pressure 504 downstream of air filter, MAP 505, and air filter resistance 506 based on inputs including atmospheric pressure, ambient temperature, engine speed, displacement volume, and volumetric efficiency. Since air filter resistance is lower than threshold 520, the controller may indicate filter prognostics such as remaining filter life.

At $T_5$, in response to the variation of MAF 503 higher than threshold $\Delta W$, observer 330 stops operation. As a result, from $T_5$ to $T_7$, air pressure downstream of air filter and the MAP are unavailable. Air filter resistance 506 maintains the estimated value from $T_5$ to $T_7$.

At $T_7$, in response to MAF 503 higher than threshold 510 and the variation less than $\Delta W$ for a duration of $\Delta d$, observer 330 starts updating air filter resistance 506. The estimated air filter resistance is higher than previous estimation from $T_4$ to $T_5$. The estimated air pressure 504 also decreased due to increased filter clogging level. In response to air filter resistance 506 higher than threshold 520, the controller may indicate filter clogging to the driver. When the filter is replaced, the air filter resistance may be reset to zero.

In this way, air filter resistance may be estimated by an observer based on one measurement of the manifold air charge value during steady engine operation. The air filter resistance is one of the system states of the observer. The filter resistance is defined to be inversely proportional to the square of a mass air flow through the air filter, and proportional to the pressure difference across the air filter. The technical effect of estimating filter resistance via an observer is that the estimation may be implemented online during engine operation, with minimal interruption of engine operation. The technical effect of estimating air filter resistance based on one measurement of the manifold air charge value is that only one sensor is required in the intake air path of the engine system. In particular, since either a MAF sensor or a MAP sensor exists in the naturally aspirated engine, no additional sensor installation is required when estimating air filter condition in these engines. The technical effect of using the filter resistance to define air filter characteristics is that the filter resistance is not sensitive to the filter geometry or filter material.

As one embodiment, a method comprises routing air through an air filter into a manifold; during steady state condition, estimating an air filter resistance based on an air charge value in the manifold, the air filter resistance being inversely proportional to the square of a mass air flow through the air filter; and indicating air filter condition based on the air filter resistance. In a first example of the method, the method further comprises estimating an air pressure immediately downstream of the air filter. A second example of the method optionally includes the first example and further includes wherein the manifold air charge value is a manifold air pressure. A third example of the method optionally includes one or more of the first and second examples, and further includes determining steady state condition based on an engine speed and an engine load. A fourth example of the method optionally includes one or more of the first through third examples, and further includes, wherein the estimation is not based on a mass air flow downstream of the air filter. A fifth example of the method optionally includes one or more of the first through fourth examples, and further includes, wherein the estimation is not based on an angle of a throttle positioned between the air filter and the manifold. A sixth example of the method optionally includes one or more of the first through fifth examples, and further includes, wherein the air filter resistance and the pressure immediately downstream of the air filter are estimated via an extended Kalman Filter, and the estimation is further based on an atmospheric pressure and an ambient temperature. A seven example of the method optionally includes one or more of the first through sixth examples, and further includes, replacing the air filter in response to the air filter resistance higher than a threshold. An eighth example of the method optionally includes one or more of the first through seventh examples, and further includes, wherein the air filter condition includes a remaining air filter life. A ninth example of the method optionally includes one or more of the first through eighth examples, and further includes wherein the air filter resistance is proportional to a pressure difference across the air filter.

As another embodiment, a method comprises sensing an air charge value in a manifold coupled to an engine, the manifold receiving air through an air filter; during steady state condition, estimating an air filter resistance and an air pressure immediately downstream of the air filter based on the sensed manifold air charge value via an observer, wherein the air filter resistance and the air pressure immediately downstream of the air filter are system states of the observer, the resistance of the air filter is inversely proportional to the square of a mass air flow through the air filter; and indicating air filter condition based on the resistance of the air filter. In a first example of the method, the manifold air charge value is a mass air flow downstream of the air filter. A second example of the method optionally includes the first example and further includes, determining steady state condition based on the mass air flow. A third example of the method optionally includes one or more of the first and second examples, and further includes, wherein the observer is an extended Kalman Filter, and system states of the observer further include a manifold air pressure. A fourth example of the method optionally includes one or more of the first through third examples, and further includes, wherein the estimation is further based on an atmospheric pressure, an ambient temperature, an engine speed, a displacement volume, and a volumetric efficiency.

As another embodiment, an engine system comprises a cylinder; a throttle upstream of the cylinder; an air filter coupled to an intake passage upstream of the throttle; a sensor downstream of the air filter for sensing an air charge value in a manifold positioned between the throttle and the cylinder; and a controller configured with computer readable instructions stored on a non-transitory memory for: during steady engine operation, estimating each and every of an air filter resistance and an air pressure immediately downstream of the air filter based on the sensed manifold air charge value, wherein the resistance of the air filter is inversely proportional to the square of a mass air flow through the air filter; and indicating air filter condition based on the resistance of the air filter. In a first example of the system, the manifold air charge value is a manifold air pressure. A second example of the system optionally includes the first example and further includes, wherein the manifold air charge value is a mass air flow downstream of the air filter and upstream of the throttle. A third example of the system optionally includes one or more of the first and second examples, and further includes, wherein during steady engine operation, a mass air flow through the air filter is the same as the mass air flow through the throttle, a mass air flow through an intake manifold, and the mass air flow downstream of the air filter and upstream of the throttle. A fourth example of the system optionally includes one or more of the first through third examples, and further includes, wherein the engine system does not include a sensor for measuring the air pressure immediately downstream of the air filter.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A method comprising:
routing air through an air filter into a manifold;
during steady state condition, estimating an air filter resistance based on an air charge value in the manifold, the air filter resistance being inversely proportional to the square of a mass air flow through the air filter; and
indicating air filter condition based on the air filter resistance,
wherein the manifold air charge value is a manifold air pressure, and wherein the estimation is not based on the mass air flow downstream of the air filter.

2. The method of claim 1, further comprising estimating an air pressure immediately downstream of the air filter.

3. The method of claim 2, wherein the air filter resistance and the air pressure immediately downstream of the air filter are estimated via an extended Kalman Filter, and the estimation is further based on an atmospheric pressure and an ambient temperature.

4. The method of claim 1, further comprising determining steady state condition based on an engine speed and an engine load.

5. The method of claim 1, wherein the estimation is not based on an angle of a throttle positioned between the air filter and the manifold.

6. The method of claim 1, wherein the air filter condition includes a remaining air filter life.

7. The method of claim 1, wherein the air filter resistance is proportional to a pressure difference across the air filter.

8. A method comprising:
sensing an air charge value in a manifold coupled to an engine, the manifold receiving air through an air filter;
during steady state condition,
estimating an air filter resistance and an air pressure immediately downstream of the air filter based on the sensed manifold air charge value via an observer, wherein the air filter resistance and the air pressure immediately downstream of the air filter are system states of the observer, the resistance of the air filter is inversely proportional to the square of a mass air flow through the air filter; and
indicating air filter condition based on the resistance of the air filter, wherein the observer is an extended Kalman Filter, and system states of the observer further include a manifold air pressure.

9. The method of claim 8, wherein the manifold air charge value is a mass air flow downstream of the air filter.

10. The method of claim 9, further comprising determining steady state condition based on the mass air flow.

11. The method of claim 9, wherein the estimation is further based on an atmospheric pressure, an ambient temperature, an engine speed, a displacement volume, and a volumetric efficiency.

12. An engine system, comprising:
a cylinder;
a throttle upstream of the cylinder;
an air filter coupled to an intake passage upstream of the throttle;
a sensor downstream of the air filter for sensing an air charge value in a manifold positioned between the throttle and the cylinder; and
a controller configured with computer readable instructions stored on a non-transitory memory for:
during steady engine operation, estimating each and every of an air filter resistance and an air pressure immediately downstream of the air filter based on the sensed manifold air charge value, wherein the resistance of the air filter is inversely proportional to the square of a mass air flow through the air filter; and
indicating air filter condition based on the resistance of the air filter,
wherein the manifold air charge value is a manifold air pressure, and wherein the engine system does not include a sensor for measuring the air pressure immediately downstream of the air filter.

13. The system of claim 12, wherein the manifold air charge value is a mass air flow downstream of the air filter and upstream of the throttle.

14. The system of claim 13, wherein during steady engine operation, a mass air flow through the air filter is the same as the mass air flow through the throttle, a mass air flow through an intake manifold, and the mass air flow downstream of the air filter and upstream of the throttle.

* * * * *